United States Patent [19]
Bradfisch et al.

[11] Patent Number: 5,985,831
[45] Date of Patent: Nov. 16, 1999

[54] **METHODS FOR CONTROLLING LEPIDOPTERANS USING *BACILLUS THURINGIENSIS* TOXINS OBTAINABLE FROM ISOLATES PS17, PS86Q3, AND HD511**

[75] Inventors: Gregory A. Bradfisch; Brian Stockhoff, both of San Diego; Judy Muller-Cohn, Del Mar, all of Calif.

[73] Assignee: Mycogen Corporation, San Diego, Calif.

[21] Appl. No.: 09/039,024

[22] Filed: Mar. 13, 1998

Related U.S. Application Data

[60] Provisional application No. 60/040,416, Mar. 13, 1997.
[51] Int. Cl.$^6$ ............................. A61K 38/00; C07K 1/00; A01N 63/00
[52] U.S. Cl. ....................... 514/12; 530/350; 424/93.461; 800/302
[58] Field of Search ............................. 435/252.3, 252.1; 530/350; 424/93.461; 514/12; 800/302

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,797,276 | 1/1989 | Herntadt et al. | 424/84 |
| 4,849,217 | 7/1989 | Soares et al. | 424/93 |
| 4,853,331 | 8/1989 | Herrnstadt et al. | 435/252.1 |
| 4,918,006 | 4/1990 | Ellar et al. | 435/69.1 |
| 4,948,734 | 8/1990 | Edwards et al. | 435/252.5 |
| 4,990,332 | 2/1991 | Payne et al. | 424/93 |
| 5,039,523 | 8/1991 | Payne et al. | 424/93 |
| 5,093,120 | 3/1992 | Edwards et al. | 424/93 |
| 5,126,133 | 6/1992 | Payne et al. | 424/93 L |
| 5,151,363 | 9/1992 | Payne | 435/252.5 |
| 5,164,180 | 11/1992 | Payne et al. | 424/93 L |
| 5,169,629 | 12/1992 | Payne et al. | 424/93 L |
| 5,185,148 | 2/1993 | Michaels | 424/93 L |
| 5,204,237 | 4/1993 | Gaertner et al. | 435/6 |
| 5,236,843 | 8/1993 | Narva et al. | 435/252.3 |
| 5,262,159 | 11/1993 | Payne et al. | 424/93 L |
| 5,262,324 | 11/1993 | Payne | 435/252.5 |
| 5,262,399 | 11/1993 | Hickle et al. | 514/12 |
| 5,268,172 | 12/1993 | Payne et al. | 424/93 L |
| 5,270,448 | 12/1993 | Payne | 530/350 |
| 5,277,905 | 1/1994 | Foncerrada et al. | 424/93 L |
| 5,281,530 | 1/1994 | Sick et al. | 435/252.3 |
| 5,286,486 | 2/1994 | Payne et al. | 424/93 L |
| 5,306,494 | 4/1994 | Payne | 424/93 L |
| 5,322,932 | 6/1994 | Narva et al. | 530/350 |
| 5,350,577 | 9/1994 | Payne | 424/93.461 |
| 5,366,892 | 11/1994 | Foncerrada et al. | 435/252.33 |
| 5,426,049 | 6/1995 | Sick et al. | 435/252.3 |
| 5,427,786 | 6/1995 | Payne et al. | 424/93.461 |
| 5,436,002 | 7/1995 | Payne et al. | 424/93.461 |
| 5,439,881 | 8/1995 | Narva et al. | 514/2 |
| 5,457,179 | 10/1995 | Foncerrada et al. | 530/350 |
| 5,468,693 | 11/1995 | Payne et al. | 435/252.3 |
| 5,506,099 | 4/1996 | Carozzi et al. | 435/6 |
| 5,554,534 | 9/1996 | Michaels et al. | 435/252.3 |
| 5,589,382 | 12/1996 | Payne et al. | 435/252.5 |
| 5,596,071 | 1/1997 | Payne et al. | 530/350 |
| 5,632,987 | 5/1997 | Payne et al. | 424/93.461 |
| 5,635,480 | 6/1997 | Payne et al. | 514/12 |
| 5,667,993 | 9/1997 | Feitelson et al. | 435/91.2 |
| 5,670,365 | 9/1997 | Feitelson | 435/252.3 |
| 5,707,619 | 1/1998 | Bradfisch et al. | 424/93.461 |
| 5,723,440 | 3/1998 | Stockhoff et al. | 514/12 |
| 5,723,758 | 3/1998 | Payne et al. | 800/205 |

FOREIGN PATENT DOCUMENTS

| | | |
|---|---|---|
| 0462721 | 12/1991 | European Pat. Off. |
| 9405771 | 3/1994 | WIPO |
| 9423036 | 10/1994 | WIPO |
| 9424264 | 10/1994 | WIPO |
| 9516778 | 6/1995 | WIPO |
| 9605314 | 2/1996 | WIPO |
| 9740162 | 10/1997 | WIPO |
| 9800546 | 1/1998 | WIPO |

OTHER PUBLICATIONS

Shevelev, A.B., M.A. Svarinsky, A.I. Karasin, Ya.N. Kogan, G.G. Chestukhina, V.M. Stepanov (1993) "Primary Structure of cry X**, the Novel δ–Endotoxin–Related Gene from *Bacillus thuringiensis* spp. *galleriae*" Federation of European Biochemical Societies 336(1):79–82.

Gleave, A.P., R.J. Hedges, A.H. Broadwell (1992) "Identification of an Insecticidal Crystal Protein from *Bacillus thuringiensis* DSIR517 with Significant Sequence differences from Previously Described Toxins" Journal of General Microbiology 138:55–62.

S.V. Smulevitch, et al. (1991) "Nucleotide Sequence of a Novel δ–Endotoxin Gene crylg of *Bacillus thuringiensis* ssp. *galleriae*" Federation of European Biochemical Societies 293(1, 2, 25, 28): 25–28.

Lambert, et al. (1996) "A *Bacillus thuringiensis* Insecticidal Crystal Protein with a High Activity against Members of the Family Noctuidae" American Society for Microbiology 62(1):80–86.

Gaertner, F.H. (1989) "Cellular Delivery Systems for Insecticidal Proteins: Living and Non–Living Microorganisms" in Controlled Delivery of Crop–Protection Agents, R.M. Wilkins, ed., Taylor and Francis, New York and London, 1990, pp. 245–255.

Schnepf, H.E., and H.R. Whiteley (1981) "Cloning and Expression of the *Bacillus thuringiensis* Crystal Protein Gene in *Escheria coli*" Proc. Natl. Acad. Sci. USA. 78:5(2893–2897).

Krieg, V.A., et al. (1983) "*Bacillus thuringiensis* var. *tenebrionis*: a new pathotype effective against larvae of Coleoptera." Z. Ang. Ent. 96:500–508.

Hofte, H., H.R. Whiteley (1989) "Insecticidal Crystal Proteins of *Bacillus thuringiensis*" Microbiological Reviews. 53:2(242–255).

Gaertner, F. and Leo Kim, (1988) "Current Applied Recombinant DNA Projects" TIBTECH. 6:4(54–57).

(List continued on next page.)

*Primary Examiner*—Robert A. Wax
*Assistant Examiner*—Devesh Srivastava
*Attorney, Agent, or Firm*—Saliwanchik, Lloyd & Saliwanchik

[57] ABSTRACT

The subject invention pertains to *B.t.* toxins and isolates active against pests.

15 Claims, No Drawings

OTHER PUBLICATIONS

Couch, T.L. (1980) "Mosquito Pathogenicity of *Bacillus thuringiensis* var. *israelensis*" in Developments in Industrial Microbiology. 22:61–76.

Beegle, C.C. (1978) "Use of Entomogenous Bacteria Agroccosystems" Developments in Industrial Microbiology. 20:97–104.

Liebert, R. et al. (1993) "Molecular characterization of dipteran–and lepidopteran–specific larvicidal proteins of *Bacillus thuringiensis* subsp. *darmstadiensis*" Abstr. Gen. Meet. Am. Soc. Microbiol. 93, Abstract Q–421, p. 423 (XP002067208).

Feitelson, J.S., et al. (1992) "*Bacillus thurigiensis*: Insects and Beyond" Bio/Technology. 10:271–275.

METHODS FOR CONTROLLING LEPIDOPTERANS USING *BACILLUS THURINGIENSIS* TOXINS OBTAINABLE FROM ISOLATES PS17, PS86Q3, AND HD511

This application claims benefit of Provisional application Ser. No. 60/040,416 filed Mar. 13, 1997.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] *TIBTECH* 6:S4–S7). Thus, isolated *B.t.* endotoxin genes are becoming commercially valuable.

Until the last fifteen years, commercial use of *B.t.* pesticides has been largely restricted to a narrow range of lepidopteran (caterpillar) pests. Preparations of the spores and crystals of *B. thuringiensis* subsp. kurstaki have been used for many years as commercial insecticides for lepidopteran pests. For example, *B. thuringiensis* var. kurstaki HD-1 produces a crystalline δ-endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *morrisoni* (a.k.a. *tenebrionis*, a.k.a. *B.t.* M-7, a.k.a. *B.t. san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.). See also Couch, T. L. (1980) "Mosquito Pathogenicity of Bacillus thuringiensis var. israelensis," *Developments in Industrial Microbiology* 22:61–76; and Beegle, C. C. (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508 describe *Bacillus thuringiensis* var. tenebrionis, which is reportedly active against two beetles in the order Coleoptera. These are the Colorado potato beetle, *Leptinotarsa decemlineata*, and *Agelastica alni*.

More recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported (Feitelson, J. S., J. Payne, L. Kim [1992] *Bio/Technology* 10:271–275). CryV has been proposed to designate a class of toxin genes that are nematode-specific. Lambert et al. (Lambert, B., L. Buysse, C. Decock, S. Jansens, C. Piens, B. Saey, J. Seurinck, K. van Audenhove, J. Van Rie, A. Van Vliet, M. Peferoen [1996] *Appl. Environ. Microbiol* 62(1):80–86) describe the characterization of a Cry9 toxin active against lepidopterans. Published PCT applications WO 94/05771 and WO 94/24264 also describe *B.t.* isolates active against lepidopteran pests. Gleave et al. ([1991] *JGM* 138:55–62), Shevelev et al. ([1993] *FEBS Lett.* 336:79–82; and Smulevitch et al. ([1991] *FEBS Lett.* 293:25–26) also describe *B.t.* toxins. Many other classes of *B.t.* genes have now been identified.

The cloning and expression of a *B.t.* crystal protein gene in *Escherichia coli* has been described in the published literature (Schnepf, H. E., H. R. Whiteley [1981] *Proc. Natl. Acad. Sci. USA* 78:2893–2897.). U.S. Pat. No. 4,448,885 and U.S. Pat. No. 4,467,036 both disclose the expression of *B.t.* crystal protein in *E. coli*. U.S. Pat. Nos. 4,990,332; 5,039,523; 5,126,133; 5,164,180; and 5,169,629 are among those which disclose *B.t.* toxins having activity against lepidopterans. PCT application WO96/05314 discloses PS86W1, PS86V1, and other *B.t.* isolates active against lepidopteran pests. The PCT patent applications published as WO94/24264 and WO94/05771 describe *B.t.* isolates and toxins active against lepidopteran pests. *B.t.* proteins with activity against members of the family Noctuidae are described by Lambert et al., supra. U.S. Pat. Nos. 4,797,276 and 4,853,331 disclose *B. thuringiensis* strain tenebrionis which can be used to control coleopteran pests in various environments. U.S. Pat. No. 4,918,006 discloses *B.t.* toxins having activity against dipterans. U.S. Pat. No. 5,151,363 and U.S. Pat. No. 4,948,734 disclose certain isolates of *B.t.* which have activity against nematodes. Other U.S. patents which disclose activity against nematodes include U.S. Pat. Nos. 5,093,120; 5,236,843; 5,262,399; 5,270,448; 5,281,530; 5,322,932; 5,350,577; 5,426,049; and 5,439,881. U.S. Pat. Nos. 5,262,159 and 5,468,636 disclose *B.t.* isolates PS157C1, PS86A1, and PS75J1 as having activity against aphids.

As a result of extensive research and investment of resources, other patents have issued for new *B.t.* isolates and new uses of *B.t.* isolates. See Feitelson et al., supra, for a review. However, the discovery of new *B.t.* isolates and new uses of known *B.t.* isolates remains an empirical, unpredictable art. U.S. Pat. No. 5,506,099 describes methods for identifying unknown *B.t.* isolates. Also, U.S. Pat. No. 5,204,237 describes specific and universal probes for the isolation of *B.t.* toxin genes.

BRIEF SUMMARY OF THE INVENTION

The subject invention concerns materials and methods useful in the control of non-mammalian pests and, particularly, plant pests. In a specific embodiment, the subject invention provides new isolates and toxins useful for the control of lepidopterans, coleopterans, and/or aphids. In preferred embodiments, these pests are selected from the group consisting of diamondback moth, Bertha armyworm, tobacco budworm, band sunflower moth, sunflower beetle, red sunflower seed weevil, canola flea beetle, sunflower stem weevil, and greenbug.

Nucleotide sequences useful according to the subject invention encode pesticidal toxins. One embodiment of the subject invention concerns plants cells transformed with at least one polynucleotide sequence of the subject invention such that the transformed plant cells express pesticidal toxins in tissues consumed by target pests. Such transformation of plants can be accomplished using techniques well known to those skilled in the art and would typically involve modification of the gene to optimize expression of the toxin in plants.

As described herein, the toxins useful according to the subject invention may be chimeric toxins produced by combining portions of multiple toxins. Also, toxins of the subject invention may be used in combination to achieve enhanced pest control.

Alternatively, the B.t. isolates of the subject invention, or recombinant microbes expressing the toxins described herein, can be used to control pests. In this regard, the invention includes the treatment of substantially intact B.t. cells, and/or recombinant cells containing the expressed toxins of the invention, treated to prolong the pesticidal activity when the substantially intact cells are applied to the environment of a target pest. The treated cell acts as a protective coating for the pesticidal toxin. The toxin becomes active upon ingestion by a target insect.

DETAILED DISCLOSURE OF THE INVENTION

The subject invention provides B.t. isolates and toxins active against diamondback moth, Bertha armyworm, tobacco budworm, band sunflower moth, sunflower beetle, red sunflower seed weevil, canola flea beetle, sunflower stem weevil, and/or greenbug.

A further aspect of the subject invention concerns novel B.t. isolates and the toxins and genes obtainable from these isolates. The novel B.t. isolates of the subject invention have been designated PS18, PS28K1, PS43A2, PS159E6, PS164H2, PS186EE, PS196Q3, PS198A2, and PS225K1.

Microorganisms useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the deposited strains are shown in Table 1.

TABLE 1

| Culture | Repository No. | Deposit Date |
| --- | --- | --- |
| PS18 | NRRL B-21954 | March 12, 1998 |
| PS28K1 | NRRL B-21955 | March 12, 1998 |
| PS43A2 | NRRL B-21956 | March 12, 1998 |
| PS159E6 | NRRL B-21958 | March 12, 1998 |
| PS164H2 | NRRL B-21959 | March 12, 1998 |
| PS186EE | NRRL B-21960 | March 12, 1998 |
| PS196Q3 | NRRL B-21961 | March 12, 1998 |
| PS198A2 | NRRL B-21962 | March 12, 1998 |
| PS225K1 | NRRL B-21963 | March 12, 1998 |
| KB6 | NRRL B-18873 | August 27, 1991 |
| KB19 | NRRL B-21964 | March 12, 1998 |

The isolates of the subject invention have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the isolates of the subject invention will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace the deposit(s) should the depository be unable to furnish a sample when requested, due to the condition of the deposit(s). All restrictions on the availability to the public of the subject culture deposits will be irrevocably removed upon the granting of a patent disclosing them.

Certain isolates which are useful according to the subject invention are available to the public by virtue of the issuance of U.S. patents. These isolates, their deposit accession number, and their date of deposit are shown in Table 2(a). The corresponding U.S. patents that disclose these isolates are shown in Table 2(b).

TABLE 2(a)

Pesticidal B.t. strains of the subject invention

| Culture | NRRL Deposit | Deposit Date |
| --- | --- | --- |
| PS17 | B-18243 | 10 AUG 87 |
| PS28Q2 | B-18888 | 25 SEP 91 |
| PS32B | B-21531 | 1 APR 96 |
| PS33F2 | B-18244 | 10 AUG 87 |
| PS50C | B-18746 | 23 JAN 91 |
| PS54G2 | B-21543 | 1 APR 96 |
| PS62B | B-18398 | 7 SEP 88 |
| PS71M3 | B-18930 | 8 JAN 92 |
| PS80JJ1 | B-18679 | 1 AUG 90 |
| PS86BB1 | B-21557 | 2 MAY 96 |
| PS86Q3 | B-18765 | 13 FEB 91 |
| PS140B2 | B-18812 | 10 APR 91 |
| PS158C2 | B-18872 | 17 SEP 91 |
| PS167P | B-18681 | 1 AUG 90 |
| PS169E | B-18682 | 1 AUG 90 |
| PS196S1 | B-18748 | 23 JAN 91 |
| PS201T6 | B-18750 | 23 JAN 91 |

The isolates HD511, HD541, and HD977 are available from the USDA-ARS NRRL Culture Collection, Peoria, Ill.

TABLE 2(b)

| U.S. Pat. No. or Publication No. | Isolate Disclosed | Sequences (of Toxin(s) and Gene(s)) Disclosed | Pesticidal Activity Disclosed |
| --- | --- | --- | --- |
| 4,849,217 | PS17 | | alfalfa weevils |
| 5,281,530 | PS17 | 17(a) and 17(b) | nematodes |
| 5,427,786 | PS28Q2 | | certain coleopteran genera, including *Hypera, Diabrotica,* and *Phyllotreta* |
| 4,849,217 | PS33F2 | | alfalfa weevils |
| 5,439,881 | PS33F2 | 33F2 | nematodes |
| 5,707,619 | PS33F2 | | various weevils |
| 5,670,365 | PS32B | | nematodes |
| 5,277,905 | PS50C | | coleopterans |
| 5,366,892 | PS50C | 50C | coleopterans |
| 5,185,148 | PS50C | | scarabs |
| 5,457,179 | PS50C | | coleopterans |
| 5,554,534 | PS50C | 50C(a) and 50C(b) | scarabs |
| 5,667,993 | PS54G2 | | nematodes |
| 5,670,365 | PS54G2 | | nematodes |
| 4,849,217 | PS62B | | alfalfa weevils |
| 5,723,440 | PS71M3 | | hemipterans |
| 4,849,217 | PS80JJ1 | | alfalfa weevils |
| WO 94/23036 | PS80JJ1 | | wireworms (click beetles) |

TABLE 2(b)-continued

| U.S. Pat. No. or Publication No. | Isolate Disclosed | Sequences (of Toxin(s) and Gene(s)) Disclosed | Pesticidal Activity Disclosed |
|---|---|---|---|
| 5,632,987 | PS80JJ1 | 80JJ1 (130 kda) | corn rootworm |
| 5,589,382 | PS80JJ1 | 80JJ1 (130 kda) | nematodes |
| 5,670,365 | PS80JJ1 | 80JJ1 (130 kda) | nematodes |
| WO 97/40162 | PS80JJ1 | 80JJ1 (14 and 44 kda) | coleopterans |
| WO 98/00546 | PS86BB1 | 86BB1(a), 86BB1(b), and 86BB1(c) | lepidopterans |
| 5,596,071 | PS86Q3 | 86Q3(a) and 86Q3(c) | ants |
| 5,427,786 | PS140E2 | | certain coleopteran genera, including *Hypera, Diabrotica,* and *Phyllotreta* |
| 5,596,071 | PS140E2 | | ants |
| 5,268,172 | PS158C2 | | lepidopterans |
| 5,723,758 | PS158C2 | 158C2(a), 158c2(b), 158C2(c), and 158C2(d) | lepidopterans |
| 5,632,987 | PS167P | | corn rootworms |
| 5,707,619 | PS167P | | various weevils |
| 5,589,382 | PS167P | 167P | nematodes |
| 5,670,365 | PS167P | 167P | nematodes |
| 5,632,987 | PS169E | | corn rootworm |
| 5,707,619 | PS169E | | various weevils |
| 5,436,002 | PS196S1 | | dipterans and corn rootworm |
| 5,707,619 | PS196S1 | | various weevils |
| 5,635,480 | PS196S1 | | dipterans and corn rootworm |
| 5,436,002 | PS201T6 | 201T6 (30 & 25 kda) | dipterans and corn rootworm |
| 5,707,619 | PS201T6 | | various weevils |
| 5,635,480 | PS201T6 | 201T6 (30 & 25 kda) | dipterans and corn rootworm |
| 5,723,440 | PS201T6 | | hemipterans |
| 5,262,324 | HD511 | | coleopterans |
| 5,286,486 | HD511 | HD511 | coleopterans |
| 5,306,494 | HD511 | | coleopterans |

These patents, with their disclosure of the indicated isolates as well as their toxins and genes, are incorporated herein by reference.

Genes and toxins

The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "purified toxin" and "isolated toxin" refer to toxins that have been affected by "the hand of man" and that are substantially free from naturally associated impurities, as the toxins would be found in their natural state. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It should be apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from *B.t.* isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. These sequences may be detectable by virtue of an appropriate label or may be made inherently fluorescentas described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) *DNA Probes,* Stockton Press, New York, N.Y., pp. 169–170. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid identity will typically be greater than 60%, preferably be greater than 75%, more preferably greater than 80%, more preferably greater than 90%, and can be greater than 95%. The amino acid homology will be highest in critical regions of the toxin which account for biological activity or are involved in the determination of three-dimensional configuration which ultimately is responsible for the biological activity. In this regard, conservative substitutions whereby an amino acid of one class is replaced with another amino acid of the same type fall within the scope of the subject invention so long as the substitution does not materially alter the biological activity of the compound. Table 3 provides a listing of examples of amino acids belonging to each class.

TABLE 3

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

Recombinant hosts

The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

A wide variety of ways are available for introducing a $B.t.$ gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Alternatively, a plant transformed to express a toxin of the subject invention can be used to contact the target pest with the toxin. Synthetic genes which are functionally equivalent to the toxins of the subject invention can also be used to transform hosts. Methods for the production of synthetic genes can be found in, for example, U.S. Pat. No. 5,380,831.

Treatment of cells

As mentioned above, $B.t.$ or recombinant cells expressing a $B.t.$ toxin can be treated to prolong the toxin activity and stabilize the cell. The pesticide microcapsule that is formed comprises the $B.t.$ toxin within a cellular structure that has been stabilized and will protect the toxin when the microcapsule is applied to the environment of the target pest. Methods for treatment of microbial cells are disclosed in U.S. Pat. Nos. 4,695,455 and 4,695,462, which are incorporated herein by reference.

Growth of cells

The cellular host containing the $B.t.$ insecticidal gene may be grown in any convenient nutrient medium, where the DNA construct provides a selective advantage, providing for a selective medium so that substantially all or all of the cells retain the $B.t.$ gene. These cells may then be harvested in accordance with conventional ways. Alternatively, the cells can be treated prior to harvesting.

The $B.t.$ cells of the invention can be cultured using standard art media and fermentation techniques. Upon completion of the fermentation cycle the bacteria can be harvested by first separating the $B.t.$ spores and crystals from the fermentation broth by means well known in the art. The recovered $B.t.$ spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Methods and formulations for pest control

Control of pests using the isolates, toxins, and genes of the subject invention can be accomplished by a variety of methods known to those skilled in the art. These methods include, for example, the application of $B.t.$ isolates to the pests (or there location), the application of recombinant microbes to the pests (or their locations), and the transformation of plants with genes which encode the pesticidal toxins of the subject invention. Recombinant microbes may be, for example, a $B.t.$, $E.$ $coli$, or Pseudomonas. Transformations can be made by those skilled in the art using standard techniques. Materials necessary for these transformations are disclosed herein or are otherwise readily available to the skilled artisan.

Formulated bait granules containing an attractant and spores and crystals of the $B.t.$ isolates, or recombinant microbes comprising the genes obtainable from the $B.t.$ isolates disclosed herein, can be applied to the soil. Formulated product can also be applied as a seed-coating or root treatment or total plant treatment at later stages of the crop cycle. Plant and soil treatments of $B.t.$ cells may be employed as liquids, wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like).

As would be appreciated by a person skilled in the art, the pesticidal concentration will vary widely depending upon the nature of the particular formulation, particularly whether it is a concentrate or to be used directly. The pesticide will be present in at least about 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Mutants

Mutants of the isolates of the invention can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

All of the U.S. patents cited herein are hereby incorporated by reference.

Following are examples which illustrate procedures for practicing the invention. These examples should not be construed as limiting. All percentages are by weight and all solvent mixture proportions are by volume unless otherwise noted.

Example 1—Culturing of B.t Isolates of the Invention

A subculture of the B.t. isolates, or mutants thereof, can be used to inoculate the following medium, a peptone, glucose, salts medium.

| Bacto Peptone | 7.5 g/l |
|---|---|
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| pH 7.2 | |
| Salts Solution (100 ml) | |
| MgSO$_4$ · 7H$_2$O | 2.46 g |
| MnSO$_4$ · H$_2$O | 0.04 g |
| ZnSO$_4$ · 7H$_2$O | 0.28 g |
| FeSO$_4$ · 7H$_2$O | 0.40 g |
| CaCl$_2$ Solution (100 ml) | |
| CaCl$_2$ · 2H$_2$O | 3.66 g |

The salts solution and CaCl$_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

The supernatant from these cultures can be used to obtain toxins according to the subject invention. Thus, the subject invention is not limited to crystal proteins; useful soluble proteins are also contemplated.

Example 2—Activity Against Diamond Back Moth (Plutella xylostella)

Certain B.t. isolates and toxins were found to be active against diamond back moth. These results are shown in Table 4.

TABLE 4

| Strain | Toxin |
|---|---|
| PS86Q3 | Cry5Ac |
| PS17 | Cry5Aa |
| HD511 | Cry7Ab2 |

Example 3—Activity Against Bertha Armyworm (Mamestra configurata)

Certain B.t. isolates and toxins were found to be active against Bertha armyworm. These results are shown in Table 5.

TABLE 5

| Strain | Toxin |
|---|---|
| HD511 | Cry7Ab |
| PS86Q3 | Cry5AC |

Example 4—Activity Against Tobacco Budworm (Heliothis virescens)

Certain B.t. isolates and toxins were found to be active against tobacco budworm.

These results are shown in Table 6.

TABLE 6

| Strain | Toxin |
|---|---|
| PS86Q3 | Cry5Ac |
| PS17 | Cry5Aa |

Example 5—Activity Against Band Sunflower Moth (Cochylis hospes)

Certain B.t. isolates and toxins have been found to be active against banded sunflower moth. The results are shown in Table 7.

TABLE 7

| Strain | Gene |
|---|---|
| PS17 | Cry5Aa |

Example 6—Activity Against Sunflower Beetle (Zygogramma exclamationis)

Certain B.t. isolates and toxins have been found to be active against sunflower beetle. These results are shown in Table 8.

TABLE 8

| Strain | Toxin |
|---|---|
| PS80JJ1 | 80JJ1 |
| PS50C | Cry8B |
| PS158C2 | 158C2(c) |

The sequence of a 1227 amino acid 158C2(c) toxin is disclosed as SEQ ID NO. 8 in U.S. Pat. No. 5,723,758. A 45 kDa toxin from PS80JJ1 is an example of a preferred toxin.

Example 7—Activity Against Red Sunflower Seed Weevil (Smicronyx fulvus)

The B.t. isolates designated PS28Q2, PS32B, PS54G2, and PS43A2 have been found to be active against red sunflower seed weevil.

Example 8—Activity Against Canola Flea Beetle (Phyllotreta cruciferae)

The B.t. isolates designated PS201T6, PS33F2, HD977, PS196Q3, PS225K1, PS164H2, KB19, PS86BB1, PS186EE, KB6, and PS198A2 have been found to be active against canola flea beetle. A cyt1B toxin and a 130 kDa toxin obtainable from PS201T6 are examples of preferred toxins for controlling Phyllotreta.

Example 9—Activity Against Greenbug (*Schizaphis graminum*)

The *B.t.* isolates designated PS159E6, PS167P, PS71M3, PS201T6, PS196SI, HD541, PS28K1, PS 18, and PS50C have been found to be active against greenbug.

Example 10—Activity Against Sunflower Spotted Stem Weevils (*Cylindrocopturus adspersus*)

The *B.t.* isolates designated PS28Q2, PS43A2, PS62B, PS86B1, PS140E2,PS169E, and PS201T6 have been found to be active against sunflower stem weevils.

Example 10—Insertion of Toxin Genes Into Plants

One aspect of the subject invention is the transformation of plants with genes encoding insecticidal toxins. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable restriction site. The resulting plasmid is used for transformation into *E. coli.* The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic *B.t.* genes for use in plants are known in the art.

Example 11—Cloning of *B.t.* Genes Into Insect Viruses

A number of viruses are known to infect insects. These viruses include, for example, baculoviruses and entomopoxviruses. In one embodiment of the subject invention, genes encoding the insecticidal toxins, as described herein, can be placed within the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J Gen. Virol* 71:1535–1544) and Martens et al. (Martens, J. W. M., G. Honee, D. Zuidema, J. W. M. van Lent, B. Visser, J. M. Vlak (1990) *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for controlling lepidopteran pests, wherein said method comprises contacting said pest with a toxin obtainable from a *Bacillus thuringiensis* isolate selected from the group consisting of PS17, PS86Q3, and HD511.

2. A method for controlling lepidopteran pests, wherein said method comprises contacting said pest with a toxin obtainable from *Bacillus thuringiensis* isolate PS17.

3. The method, according to claim 2, wherein said toxin is a cry5Aa toxin.

4. The method, according to claim 2, wherein said toxin is expressed by a transformed plant.

5. The method, according to claim 2, wherein said lepidopteran pest is *Plutella xylostella*.

6. The method, according to claim 2, wherein said lepidopteran pest is *Heliothis virescens*.

7. The method, according to claim 2, wherein said lepidopteran pest is *Cochylis hospes*.

8. A method for controlling a lepidopteran pest, wherein said method comprises contacting said pest with a toxin obtainable from *Bacillus thuringienis* isolate PS86Q3.

9. The method, according to claim 8, wherein said toxin is a Cry5Ac toxin.

10. The method, according to claim 8, wherein said toxin is expressed by a transformed plant.

11. The method, according to claim 8, wherein said pest is selected from the group consisting of *Plutella xylostella, Mamestra configurata,* and *Heliothis virescens*.

12. A method for controlling lepidopteran pests, wherein said method comprises contacting said pest with a toxin obtainable from *Bacillus thuringiensis* isolate HD511.

13. The method, according to claim 12, wherein said toxin is expressed by a transformed plant.

14. The method, according to claim 12, wherein said lepidopteran pest is *Plutella xylostella*.

15. The method, according to claim 12, wherein said lepidopteran pest is *Mamestra configurata*.

* * * * *

UNITED STATES PATENT AND TRADEMARK OFFICE
CERTIFICATE OF CORRECTION

PATENT NO. : 5,985,831

DATED : November 16, 1999

INVENTOR(S) : Bradfisch et al.

It is certified that error appears in the above-identified patent and that said Letters Patent is hereby corrected as shown below:

Column 4 (Table 2(a), 12th line under Culture): "PS140B2" should read --PS140E2--.

Column 6, line 35: "fluorescentas" should read --fluorescent as--.

Signed and Sealed this

Third Day of April, 2001

Attest:

NICHOLAS P. GODICI

Attesting Officer

Acting Director of the United States Patent and Trademark Office